(12) United States Patent
Hoffenblum

(10) Patent No.: US 12,370,211 B2
(45) Date of Patent: **\*Jul. 29, 2025**

(54) FORMULATIONS OF MAGNESIUM CHLORIDE TO TREAT MUSCLE SPASM, STRAIN AND SPRAIN

(71) Applicant: FLEX-IT MG LLC, Traverse City, MI (US)

(72) Inventor: Harvey Hoffenblum, Troy, MI (US)

(73) Assignee: FLEX—IT MG LLC, Traverse City, MI (US)

( * ) Notice: Subject to any disclaimer, the term of this patent is extended or adjusted under 35 U.S.C. 154(b) by 547 days.

This patent is subject to a terminal disclaimer.

(21) Appl. No.: 17/825,581

(22) Filed: May 26, 2022

(65) Prior Publication Data

US 2022/0280559 A1    Sep. 8, 2022

Related U.S. Application Data

(63) Continuation-in-part of application No. 16/669,982, filed on Oct. 31, 2019, now Pat. No. 11,369,630.

(60) Provisional application No. 62/753,441, filed on Oct. 31, 2018.

(51) Int. Cl.
    *A61K 33/00*     (2006.01)
    *A61K 36/886*    (2006.01)
    *A61K 47/10*     (2017.01)

(52) U.S. Cl.
    CPC ............ *A61K 33/00* (2013.01); *A61K 36/886* (2013.01); *A61K 47/10* (2013.01)

(58) Field of Classification Search
    CPC ...... A61K 33/00; A61K 36/886; A61K 47/10; A61K 9/0014; A61K 31/047; A61K 31/77; A61K 33/06
    See application file for complete search history.

(56) References Cited

U.S. PATENT DOCUMENTS

| | | | |
|---|---|---|---|
| 4,041,154 A | 8/1977 | Helbig et al. | |
| 6,051,236 A | 4/2000 | Portman | |
| 9,717,757 B1* | 8/2017 | Gasque, Jr. | ........... A61K 31/122 |
| 10,391,121 B2 | 8/2019 | Chan | |
| 2005/0232980 A1* | 10/2005 | Chen | ................... A61K 31/737 |
| | | | 424/448 |
| 2017/0049694 A1* | 2/2017 | Maalawy | ............. A61K 9/1271 |
| 2018/0318342 A1 | 11/2018 | Chan | |

\* cited by examiner

*Primary Examiner* — Snigdha Maewall
(74) *Attorney, Agent, or Firm* — Technology Law PLLC; Karen L Kimble

(57) ABSTRACT

The present invention describes the use of a pharmaceutically-acceptable formulation of magnesium chloride as the active ingredient to treat muscle spasm, strain and sprain in an animal or human.

10 Claims, No Drawings

FORMULATIONS OF MAGNESIUM CHLORIDE TO TREAT MUSCLE SPASM, STRAIN AND SPRAIN

FIELD OF THE INVENTION

The present invention concerns the preparation and use of a roll-on, gel, cream or spray formulation for treating muscle spasms, strains, and sprains in animals or humans.

BACKGROUND OF THE INVENTION

Magnesium and calcium are two ions that need to be in a proper equilibrium in order for the muscle cell to function properly. Dehydration, often due to excessive exercise, sweating from exercise or heat or diuretic ingestion such as with coffee or alcohol, can cause a loss of intracellular magnesium.

Muscle anatomy basically consists of two components, Myosin and Actin sheaths. When a muscle is in a relaxed state, these two sheaths glide over each other with little or no resistance. When a nerve impulse activates the muscle, the two muscle sheaths contract in a ratchet like fashion.

Calcium ion is needed to sustain this ability of the muscle to contract for the ratchet action. Too much calcium ion can cause stiff muscles or "the rusty ratchet effect." Magnesium is nature's physiologic calcium blocker and replaces calcium in the contraction cycle and causes relaxation of the muscle.

Current remedies for "stiff" muscles include using Epsom salts (i.e., $MgSO_4 \cdot 7\ H_2O$). Magnesium sulfate came into medical use at least as early as 1618. It is on the World Health Organization's List of Essential Medicines, the most effective and safe medicines needed in a health system. Various uses of Epsom salts include treatment for: arthritis pain and swelling; bruises and sprains; fibromyalgia, a condition that makes your muscles, ligaments, and tendons hurt, and causes tender points throughout your body; psoriasis, a disease that causes red, itchy, scaly skin; sore muscles after working out; soreness from diarrhea during chemotherapy; sunburn pain and redness; and tired, swollen feet.

The usual method of treating muscles with Epsom salts is to take a warm bath with Epsom salts added. However, magnesium salts that form in the bath water from the Epsom salts can act as an astringent and can cause dry skin so a hydrating lotion is often used after the bath.

Clearly, a formulation that provides the benefits of Epsom salts but can be used without the need to take a warm bath, could be more easily used anywhere, and conveniently taken with you is needed.

BRIEF SUMMARY OF THE INVENTION

The present invention is the use of magnesium chloride in a formulation, used for the purpose of the magnesium sulfate, but also formulated to meet other needs has now been made by this invention. Magnesium sulfate is soluble in water at 26.9 g/100 mL. In contrast, magnesium chloride is a highly water soluble, 54.2 g/100 mL. A potent form of magnesium ion for fast-acting topical uses is needed. Magnesium chloride is more easily absorbed and utilized by the body than other forms or salts of magnesium. Magnesium chloride is selected over other possible salts because of its clinical and pharmacological effects, and its lower tissue toxicity as compared to magnesium sulfate. Other advantages of magnesium chloride are discussed in the Detailed Description of this application.

Other ingredients are used in the present formulation to increase the absorption of magnesium ions into the muscle. Some additives are excipients such as non-ionic surfactants, water-soluble glycols, such as polyethylene glycol (PEG) or propylene glycol (PG), and aloe used to treat dry skin—because magnesium salts can act as an astringent and can cause dry skin. These water-soluble glycols are used to increase the magnesium concentration present in a roll-on formulation to be applied smoothly without causing the ball of the roll-on to be sticky or not clogging for the spray device. Also, these water-soluble glycols allow for a greater concentration of the formulation to flow through the device. When desired, an aroma additive can optionally be added to the present formulation to combat the unpleasant body order from sweating when the formulation is applied after exercise.

The present invention also provides a method for the treatment of an animal or human in need of treatment for muscle spasm, strain or sprain by use of a pharmaceutically-acceptable formulation of magnesium chloride. The formulation is a liquid and may be applied in any suitable manner such as a spray or roll-on application, with the roll-on preferred. The preferred components of the formulation are discussed below.

DETAILED DESCRIPTION OF THE INVENTION

The increased solubility of this formulation where the active ingredient is magnesium chloride ($MgCl_2$), compared to Epsom salts ($MgSO_4$), allows for a higher concentration of the magnesium ion to penetrate into the muscle.

In a review article (Adrian C. Williams and Brian W. Berry, "Penetration enhancers", *Advanced Drug Delivery Reviews*, 56 (2004), 603-618) the penetration enhancers use is discussed. It is well known that improving transdermal drug delivery often advocates penetration enhancers (also called sorption promoters or accelerants). These agents penetrate into skin to reversibly decrease the barrier resistance to drugs. Numerous compounds have been evaluated for penetration enhancing activity, including sulphoxides (such as dimethylsulphoxide, DMSO), Azones (e.g. laurocapram), pyrrolidones (for example 2-pyrrolidone, 2P), alcohols and alkanols (ethanol, or decanol), glycols (for example propylene glycol (PG), polypropylene glycol, polyethylene glycol (PEG) and ethylene glycol, a common excipient in topically applied dosage forms), surfactants (also common in dosage forms) and terpenes. Some of these agents are more useful than others or work better in some formulations.

Many potential sites and modes of action have been identified for agents that serve as such skin penetration enhancers. Examples of some sites are the intercellular lipid matrix in which the accelerants may disrupt the packing motif, the intracellular keratin domains or through increasing drug partitioning into the tissue by acting as a solvent for the permeant within the membrane. Further potential mechanisms of action, for example with the enhancers acting on desmosomal connections between corneocytes or altering metabolic activity within the skin, or exerting an influence on the thermodynamic activity/solubility of the drug in its vehicle are also thought feasible.

The present formulation also includes other additives to aid in the penetration of the muscle, the flow of the formulation, provide aroma, soothing ingredients such as aloe, and excipients to make the formulation apply as a roll-on or spray; especially useful is the roll-on formulation for direct application to the desired site.

Epsom salt is not very soluble in water (26.9 g/100 mL), whereas the present formulation with $MgCl_2$ is much more soluble in water (4.2 g/100 mL). This improved solubility is important in the present formulation. Other forms of magnesium salts have different solubility and toxic concerns.

Other known $MgCl_2$ preparations, commonly known as magnesium oils, are sticky to touch and leave a residue on the skin once they are applied. Because they do not contain the water-soluble glycol as an excipient, their absorbency into the muscle is less effective. These known preparations also do not contain aloe, which is needed to prevent dry skin caused from the magnesium ions from $MgC_2$.

Because the present formulation is a roll-on formulation or spray, it dries quickly, whereas the known formulations are wet and gooey and may not dry at all or only after a longer time interval. Creams or gels frequently require that they are rubbed in and can make the person's hands gooey or sticky. The present roll-on formulation is very convenient to take with you and apply with no sticky hands, without soiling the clothes or having time delays to have it dry. The amount applied varies depending on the site of the muscle area having the spasm, strain or sprain.

The present invention relates to a method for the treatment of an animal or human in need of treatment for muscle spasm, strain or sprain by use of a pharmaceutically-acceptable formulation consisting of applying to the animal or human, an effective amount of an aqueous roll-on formulation of: (a) about 45-55% w/v (weight/volume) of magnesium chloride in the total formulation, (b) a water-soluble glycol selected from propylene glycol or polyethylene glycol of about 0.1% to about 0.3% w/v in the total formulation, (c) aloe from about 5% to about 6% v/v (volume/volume) of the total formulation, (d) optionally a counter irritant or aroma ingredient from about 12% to about 16% v/v of the total formulation, and (e) distilled water, in an amount to equal !00% v/v of the total formulation.

In this formulation counter irritant or aroma ingredient means menthol or camphor or other aromatic oils.

The following formulations are included within the present formulation.

A present roll-on formulation is applied from a device having a net weight of components of the formulation of about 130 g or 3 oz. comprising the following pharmaceutically-acceptable components:
- a) $MgCl_2$ at about 60 g to about 65 g or about 45% to about 50% w/v (weight/volume) of the total formulation;
- b) A water-soluble glycol of propylene glycol or polyethylene glycol of about 0.1% to about 0.2% w/v of the total formulation;
- c) Aloe of about 5% to about 6% v/v of the total formulation; and
- d) Distilled water to equal 100% v/v of the total formulation.

The roll-on formulation is a liquid at room temperature. These formulations have an estimated shelf life of about 2 years.

The present above formulation for a 3 oz device described above is prepared by:
- A. Adding the $MgCl_2$ to distilled water in a vessel and heating, optionally stirring or shaking the mixture, until the $MgCl_2$ is dissolved;
- B. After cooling the solution from step A to about room temperature, transferring the $MgCl_2$ solution to the individual dispensing device(s);
- C. Adding the water-soluble glycol of b) in the formulation described above to each device;
- D. Microwave or heating each device to cause the water-soluble glycol to complex with the $MgCl_2$ in solution;
- E. After the device cools to about room temperature, adding the aloe of c) in the formulation described above to each device; and
- F. Adding distilled water as needed d) to obtain 100% of the formulation described above to each device; and
- G. Final assembly of the device and labeling.

When a larger batch is wanted the formulation is prepared by the following process:
- A. Add 960 mL of distilled water into a large vessel;
- B. Add 1800 g of $MgCl_2$ to the distilled water in step A;
- C. Heat the solution from step B over medium heat until $MgCl_2$ is dissolved;
- D. To the hot mixture from step C, add 21 g of the water-soluble glycol of step 6 b) above to the mixture to stabilize the $MgCl_2$;
- E. After cooling the step D mixture to about room temperature, add 120 mL of aloe and stir until uniformly distributed;
- F. Optionally adding the counter irritant or aroma ingredient to each device in step E; and
- H. Final assembly of 24 devices of 90 mL each and labeling.

The heating can be done by microwave or other conventional means.

Because of its improved properties, the present formulation of $MgCl_2$ could be used in a device like a spray, including an aerosol spray. The method of making such sprays from the above components is well known in this art.

General Procedure

In the following examples, the data is antidotal but told to the inventor. In some instances, he has actual knowledge of the before and after statements.

Materials and Methods

The various components were purchased commercially. These components can be purchased from any suitable source.

$MgCl_2$ from Pure Organic LLC
Propylene glycol from Blin's Farm & Fleet
Polyethylene glycol from CVS Health
Aloe from Warren laboratories LLC
Counter irritant or aroma ingredients from Walgreens
Distilled water from Meijer The product was tested as a roll-on application using the above formulation made by the process as described above.

Examples

Example 1:

A 35 year old male, who is an avid kick boxer, takes whirlpool baths with Epsom salts after competition to relieve his pain. After using this present preparation, he no longer adds Epsom salt to his whirlpool, but prefers to apply the present preparation directly to his sore muscles.

Example 2:

A 45 year old woman, who is an occupational therapist, finds it difficult to work because of severe chronic pain in her deltoid muscles. Being under a doctor's care, the only remedy that seemed to help her was prescription strength lidocaine patches. After using the present preparation, the pain and stiffness are now gone.

Example 3:

A 55 year old woman, who is a housekeeper, had a rotator cuff injury. After surgery she was incapacitated and in a lot of pain. Using the present preparation immediately mitigated her pain. Over one month of use she was able to return to work.

Example 4:

A 65 year old retired nurse was in worsening chronic shoulder pain. Although palliative treatments such as oral NSAIDS's and GABA agonists temporally helped, nothing was slowing the progression of the pain. One day she realized that this worsening chronic pain was now preventing her from combing her hair. After using the present preparation, the pain started to subside. Now after several months of use, she is pain free and has recovered almost full range of motion.

Example 5:

A 30 year old male is a recreational runner but has a history of chronic muscle injury due to his forgetfulness to warm up before his runs. Now he uses the present preparation before his runs and is without muscle injury.

Example 6:

A 72 year old male who had an amputation of his leg below the knee due to diabetes needed crutches to be mobile. Pressure on his palms due to the weight from using crutches caused severe cramping. The application of this present formulation relieved the cramping so he can use his crutches without pain.

Example 7:

A 73 year old female who has night time leg cramps that are so severe that these cramps wake her up. After applying the present formulation within 15 minutes thereafter she could go back to sleep without cramps.

Example 8:

A 55 year old male golf instructor gets cramps in his right forearm from swinging a club and affects his golf game. He uses the present formulation to successfully mitigate these cramps.

Example 9:

A 35 year old female sports enthusiast applies the present formulation prophylactically before going out on the water on a stand up paddle board to prevent calf muscle pain. It works as no cramping happens.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. All such modifications that fall within the spirit and broad scope of the appended claims are included.

What is claimed is:

1. A method for the treatment of an animal or human in need of treatment for muscle spasm, strain or sprain by use of a pharmaceutically-acceptable formulation consisting of applying to the animal or human, as a roll-on, an effective amount of an aqueous formulation of:
   (a) about 45-55% w/v (weight/volume) of magnesium chloride in the total formulation,
   (b) a water-soluble glycol selected from propylene glycol or polyethylene glycol of about 0.1% to about 0.3% w/v in the total formulation,
   (c) aloe from about 5% to about 6% v/v (volume/volume) of the total formulation,
   (d) optionally one or more of a counter irritant or aroma ingredient from about 12% to about 16% v/v of the total formulation, and
   (e) distilled water, in an amount to equal 100% v/v of the total formulation.

2. The method of claim 1, wherein the formulation is non-sticky to the touch or clothing.

3. The method of claim 1, wherein the formulation dries on the skin in a about 1-2 minutes.

4. The method of claim 1, wherein the roller-ball does not cake or clog upon repeated use.

5. The method of claim 1, wherein the formulation is applied 1-2 times to obtain the effect without massage of the area.

6. The method of claim 1, wherein the counter irritant or aroma ingredient is menthol or camphor or other aromatic oils.

7. The method of claim 1, wherein the formulation used in the method has a net weight of components of about 130 g or 3 oz. consisting of the following pharmaceutically-acceptable components:
   (a) $MgCl_2$ at about 60 g to about 65 g or about 45% to about 50% w/v (weight/volume) of the total formulation;
   (b) A water-soluble glycol of propylene glycol or polyethylene glycol of about 0.1% to about 0.2% w/v of the total formulation;
   (c) Aloe of about 5% to about 6% v/v of the total formulation; and
   (d) Distilled water to equal 100% v/v of the total formulation.

8. A process for preparing the formulation as defined in claim 7 comprising steps:
   A. Adding the $MgCl_2$ of claim 7 a) to distilled water in a vessel and heating, optionally stirring or shaking the mixture, until the $MgCl_2$ is dissolved;
   B. After cooling the solution from step A to about room temperature, transferring the $MgCl_2$ solution to the individual dispensing device(s);
   C. Adding the water-soluble glycol of claim 7 b) to each device;
   D. Microwave or heating each device to cause the glycol to complex with the $MgCl_2$ in solution;
   E. After the device cools to about room temperature, adding the aloe of claim 7 c) to each device;
   F. Adding the distilled water of claim 7 d) to each device; and
   H. Final assembly of the single device of 3 ounces of formulation and labeling.

9. A process for preparing the formulation as defined in claim 1 comprising steps:
   A. Add 980 mL of distilled water into a large vessel;
   B. Add 1800 g of $MgCl_2$ to the distilled water in step A;
   C. Heat the solution from step B over medium heat until $MgCl_2$ is dissolved;
   D. To the hot mixture from step C, add 21 g of the water-soluble glycol selected from propylene glycol or polyethylene glycol to the mixture to stabilize the $MgCl_2$;
   E. After cooling the step D mixture to about room temperature, add 120 mL of aloe and stir until about uniformly distributed and distribute into the devices;
   F. Optionally adding any counter irritant or aroma ingredient to each device in step E; and
   G. Final assembly of 24 devices of 90 mL each of formulation and labeling.

10. The method of claim 1, wherein the water-soluble glycol is polyethylene glycol.

* * * * *